US006900317B2

(12) United States Patent
Trunk et al.

(10) Patent No.: US 6,900,317 B2
(45) Date of Patent: May 31, 2005

(54) SALTS OF THE CGRP ANTAGONIST BIBN4096 AND INHALABLE POWDERED MEDICAMENTS CONTAINING THEM

(75) Inventors: Michael Trunk, Ingelheim (DE); Claudius Weiler, Ingelheim-Grosswinternheim (DE)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 0 days.

(21) Appl. No.: 10/365,327

(22) Filed: Feb. 12, 2003

(65) Prior Publication Data

US 2003/0191068 A1 Oct. 9, 2003

Related U.S. Application Data

(60) Provisional application No. 60/362,268, filed on Mar. 6, 2002.

(30) Foreign Application Priority Data

Feb. 19, 2002  (DE) ........................................ 102 06 770

(51) Int. Cl.$^7$ ........................................... C07D 403/14
(52) U.S. Cl. ..................................................... 544/284
(58) Field of Search ...................... 514/252.17; 544/284

(56) References Cited

U.S. PATENT DOCUMENTS

| | | | |
|---|---|---|---|
| 3,634,582 A | | 1/1972 | Hartley et al. |
| 4,396,616 A | * | 8/1983 | Harris et al. ................. 514/183 |
| 6,165,506 A | | 12/2000 | Jain et al. |
| 6,344,449 B1 | * | 2/2002 | Rudolf et al. .......... 514/211.05 |
| 6,509,005 B1 | | 1/2003 | Peart et al. |
| 6,518,239 B1 | | 2/2003 | Kuo et al. |
| 6,521,609 B1 | | 2/2003 | Doods et al. |

FOREIGN PATENT DOCUMENTS

| | | |
|---|---|---|
| DE | 1 792 207 | 11/1971 |
| WO | WO 98/11128 A | 3/1998 |
| WO | WO 00/00176 A1 | 1/2000 |
| WO | WO 00/24362 A | 5/2000 |
| WO | WO 00/45878 A2 | 8/2000 |
| WO | WO 01/10425 A | 2/2001 |
| WO | WO 01/32144 A | 5/2001 |
| WO | WO 02/056866 A1 | 7/2002 |

OTHER PUBLICATIONS

Dark, Graham, "On–Line Medical Dictionary" [online] Nov. 18, 1997 [retrived on Apr. 1, 2004]. Retrived from the Internet: <http://cancerweb.ncl.ac.uk/cgi–bin/omd?micronise>.*
Doods, H. et al; "Pharmacological profile of BIBN4096BS, the first selective small molecule CGRP antagonist"; British Journal of Pharmacology, 129 (3); 2000, pp. 420–423.
Abstract: 1966–36583F [00] WPIDS (for DE 1 792 207).
Jung, J. et al; "Particle Design Using Supercritical Fluids"; J. Supercrit. Fluids 20 (2001), pp. 179–219.
Gallager, M. P. et al; "Gas Antisolvent Recrystallization: New Process To Recrystallize Compounds Insoluable in Supercritical Fluids", Am. Chem. Soc. (1989), pp. 334–354.

(Continued)

Primary Examiner—Thomas C. McKenzie
(74) Attorney, Agent, or Firm—Michael P. Morris; Mary-Ellen M. Devlin; Alan R. Stempel (57) ABSTRACT

The invention relates to salts of the active substance base 1-[N$^2$-[3,5-dibromo-N-[[4-(3,4-dihydro-2(1H)-oxoquinazolin-3-yl)-1-piperidinyl]carbonyl]-D-tyrosyl]-L-lysyl]-4-(4-pyridinyl)-piperazine [BIBN4096] of formula I, the preparation thereof, a process for preparing an inhalation powder containing a salt of the active substance BIBN4096 as well as the inhalation powders which can be obtained by the process.

20 Claims, 4 Drawing Sheets

Scanning electron micrograph of microparticles of BIBN4096 hydrochloride, prepared by the process according to the invention (aqueous spray solution; Example 3).

OTHER PUBLICATIONS

Dixon, D. J. et al; "Polymeric Materials Formed By Precipitation With Compressed Fluid Antisolvent", AlChE Journal (1993) vol. 39(1), p. 127.

Maa, Y. F. et al; "Effect of Spray Drying and Subsequent Processing Conditions on Residual Moisture Content and Physical/Biochemical Stability of Protein Inhalation Powders"; Pharmaceutical Research (1998) 15, No. 5; pp. 768–775.

Vidgren, M. T. et al; "Comparison of physical and inhalation properties of spray–dried and mechanically micronized disodium cromoglycate*"; Int. J. Pharmaceutics, (1987), 35, pp. 139–144.

Niven, R. W. et al; "Pulmonary Delivery of Powders and Solutions Containing Recombinant Human Granulocyte Colony–Stimulating Factor (rhG–CSF) to the Rabbit"; Pharmaceutical Research (1994) 11, No. 8, pp. 1101–1109.

* cited by examiner

Figure 1: Scanning electron micrograph of microparticles of BIBN4096 hydrochloride, prepared by the process according to the invention (aqueous spray solution; Example 1).

Figure 2: Scanning electron micrograph of microparticles of BIBN4096 hydrochloride, prepared by the process according to the invention (aqueous spray solution; Example 2).

Figure 3: Scanning electron micrograph of microparticles of BIBN4096 hydrochloride, prepared by the process according to the invention (aqueous spray solution; Example 3).

Figure 4: Scanning electron micrograph of microparticles of BIBN4096 hydrochloride, prepared by the process according to the invention (aqueous spray solution; Example 4).

SALTS OF THE CGRP ANTAGONIST BIBN4096 AND INHALABLE POWDERED MEDICAMENTS CONTAINING THEM

RELATED APPLICATIONS

Benefit of U.S. Provisional Application Ser. No. 60/362,268, filed on Mar. 6, 2002 is hereby claimed.

FIELD OF THE INVENTION

The invention relates to salts of the substance 1-[$N^2$-[3,5-dibromo-N-[[4-(3,4-dihydro-2(1H)-oxoquinazolin-3-yl)-1-piperidinyl]carbonyl]-D-tyrosyl]-L-lysyl]-4-(4-pyridinyl)-piperazine[BIBN4096] of formula I, which are stable in their amorphous state under normal conditions (T<50° C., relative humidity <75%), processes for preparing them, the use of these salts for preparing a pharmaceutical composition of the inhalation powder type, particularly for preparing a pharmaceutical composition with CGRP-antagonistic properties, as well as a process by means of which in a single step the thermodynamically stable or stabilised salts of the active substance in their amorphous state can be processed to form microparticles.

In the process according to the invention the salts are obtained in the form of spherically nanostructured microparticles which are suitable for preparing inhalation powders in which no other excipients or additives (carrier materials) are required, in order to obtain a powder which can be handled on an industrial scale, which can be further processed directly and has excellent properties in terms of dispersability and is sufficiently easy to process with regard to its cohesive properties. In another aspect the invention relates to the inhalation powders which may be obtained using the process according to the invention.

Formula I:

PRIOR ART

BIBN4096 is a highly effective CGRP antagonist for the treatment of migraine, which is described in U.S. Pat. No. 6,344,449. It cannot be administered orally using conventional preparations as the substance has only limited bioavailability by oral route both in the form of the active substance base and also in the form of its salts.

In the case of inhalation powders, inhalable powders which are packed into suitable capsules (inhalettes) are delivered into the lungs by means of powder inhalers. Alternatively, they may be inhaled by the use of suitable powdered inhalable aerosols which may contain, for example HFC134a, HFC227 or mixture thereof as propellant gas.

The microparticles of the pure active substance are administered through the airways to the surface of the lung, e.g. in the alveoli, by the inhalation process. These particles settle on the surface and can only be absorbed in the body after the dissolution process by active and passive transporting processes.

Inhalation systems are known in the literature wherein the active substance is present either as a micronised suspension in a suitable solvent system as the carrier, or in the form of a dry powder.

Usually, inhalation powders are prepared e.g. in the form of capsules for inhalation based on the general teaching as described in DE-A-179 22 07, using the chemically most stable form of the active substance. Pharmaceutical preparations prepared by mixing a finely divided medicament with a coarser carrier medium are dispersed in an air current by a so-called "powder flow method" using the suction mode of the inhaler as the main energy source.

A critical factor in multi-substance systems of this kind is the uniform distribution of the pharmaceutical composition in the powder mixture. Moreover, the carrier results in additional stress on the lungs as well as the occurrence of undesirable interactions, which may lead to problems of compatibility.

One significant aspect of the administration of the active substance by inhalation is that only particles of a specific aerodynamic size enter the target organ, namely the lungs. The particle size of these particles destined for the lungs (inhalable fraction) is in the submicron range. Such particles are conventionally produced by micronisation (grinding in an air stream). As a result, such particles may often be of complex composition in terms of their crystal properties as a result of this mechanical step. Similarly, the geometric form of the particles of starting material also determines the morphological properties of the micronised material.

Apart from the jet grinding process, the airstream grinding process being of particular significance, it is also possible to produce a suitable micronised product by alternative methods. Suitable micronising processes for preparing microparticles in the submicron range include, for example, the precipitation method including the processes in which the active substance can be precipitated as a non-crystalline (amorphous) solid by evaporating the solvent beyond its maximum solubility, precipitation by means of supercritical gases, such as the RESS or PGSS process (J. Jung, M.

Perrut: *Particle Design Using Supercritical Fluids,* J. Supercrit. Fluids 20 (2001), 179–219), the GASR process (M. P. Gallager et al.: *Gas Antisolvent Recrystallization,* Am. Chem. Soc. (1989)), the PCA process (D. J. Dixon, K. P. Johnston: *Polymeric Materials Formed by Precipitation with compressed Fluid Antisolvent,* AIChE Journal (1993, Vol. 39(1), 127), freeze-drying, spray drying or a combination of several of the abovementioned processes.

It is known from the literature that lung-bound particles measuring between 0.5 µm and 10 µm, preferably between 0.5 µm and 6 µm, can be produced by spray-drying. Industrially usable formulations can normally be prepared from spray-dried particles of this kind using the method mentioned above (DE-A-179 22 07) which have sufficient dispersibility for medical use (inhalation) [Y.-F. Maa, P.-A. Ngyuyen, J. D. Andya, N. Dasovich, T. D. Sweeny, S. J. Shire, C. C. Hsu, Pharmaceutical Research, 15, No. 5 (1998), 768–775; M. T. Vidgrén, P. A. Vidgrén, T. P. Paronen, Int. J. Pharmaceutics, 35 (1987), 139–144; R. W. Niven, F. D. Lott, A. Y. Ip, J. M. Cribbs, Pharmaceutical Research, 11, No. 8 (1994), 1101–1109].

In addition to these examples there are other methods of production, proposed by pharmaceutical companies in particular, based on spray-drying processes, which describe special formulations for inhalation powders.

Apart from the requirements set out hereinbefore, it should generally be borne in mind that any change to the solid state of a pharmaceutical composition which can improve its physical and chemical stability as well as its technical qualities provides a considerable advantage over less stable forms of the same medicament.

STATEMENT OF THE PROBLEM

The complex objective of the present invention was primarily to provide a bioavailable formulation for the salts of the highly effective CGRP antagonist BIBN4096. The formulation according to the invention should have a rapid onset of activity for the treatment of acute pain or, in the case of migraine, pain with a very sudden onset. This means that rapid absorption of the active substance and a fast rise in the plasma level must be ensured.

Therefore, the aim was further to provide novel, sufficiently stable salts of BIBN4096 which are particularly suitable for preparing inhalation powders that can be used directly without the addition of carrier materials, in order to avoid the consequent problems that arise from the administration of multi-substance mixtures. The individual, spherically nanostructured microparticles of the powder should therefore be suitable for administration by inhalation, both in their particle size (aerodynamics) and in their dispersibility. Moreover the formulation should be capable of being prepared in as few steps as possible and the powder should be reasonably easy to process on an industrial scale in terms of its cohesive properties.

DESCRIPTION OF THE INVENTION

A rapid onset of activity for the treatment of acute pain and for achieving a high plasma level of the salts of the active substance BIBN4096 within the shortest possible time can best be achieved, apart from by intravenous administration, via the lungs as the receiving organ.

Within the scope of the present invention it has now, surprisingly, been found that the salts of BIBN4096 may be made sufficiently bioavailable by administering them by inhalation. It has been found that when the active substance is administered by inhalation in the form of spherically nanostructured microparticles a bioavailability of about 60% based on the fine fraction of the formulation (corresponding to FPD determined according to USP 24 Suppl. 2000) can be achieved.

A first object of the present invention is thus the acid addition salts of the active substance base 1-[$N^2$-[3,5-dibromo-N-[[4-(3,4-dihydro-2(1H)-oxoquinazolin-3-yl)-1-piperidinyl]carbonyl]-D-tyrosyl]-L-lysyl]-4-(4-pyridinyl)-piperazine [BIBN4096] of formula (I).

A preferred first object is those acid addition salts, which are selected from among 1-[$N^2$-[3,5-dibromo-N-[[4-(3,4-dihydro-2(1H)-oxoquinazolin-3-yl)-1-piperidinyl]carbonyl]-D-tyrosyl]-L-lysyl]-4-(4-pyridinyl)-piperazine hydrochloride, sulphate, phosphate, hydrobromide, carbonate, methanesulphonate, p-toluenesulphonate, nitrate, citrate, malate, tartrate, lactate, succinate, gluconate, acetate, formate, propionate, capronate, oxalate, maleate, fumarate, mandelate and hydroxysuccinate, while the 1-[$N^2$-[3,5-dibromo-N-[[4-(3,4-dihydro-2(1H)-oxoquinazolin-3-yl)-1-piperidinyl]carbonyl]-D-tyrosyl]-L-lysyl]-4-(4-pyridinyl)-piperazine hydrochloride, sulphate and hydrobromide are particularly preferred and the 1-[$N^2$-[3,5-dibromo-N-[[4-(3,4-dihydro-2(1H)-oxoquinazolin-3-yl)-1-piperidinyl]carbonyl]-D-tyrosyl]-L-lysyl]-4-(4-pyridinyl)-piperazine-hydrochloride is most particularly preferred.

The abovementioned salts are in a stable amorphous state under normal conditions (T<50° C., relative humidity <75%).

They may be prepared analogously to methods known from the literature. For example, the salts may be obtained by dissolving the active substance base in a solvent such as water or an aqueous buffer system with a pH between 4 and 8, preferably between 6 and 8, adding the corresponding acid in excess, preferably by adding 0.9 to 1.1 equivalents of the corresponding acid, and subsequently eliminating the solvent, e.g. under reduced pressure using a rotary evaporator, by freeze-drying, by spray-drying or comparable methods in which the solvent is removed from the solution. Other methods are those wherein the substance can be obtained as a solid by concentrating it in the solvent to achieve supersaturation.

A second object of the invention is thus a process for preparing the abovementioned acid addition salts, characterised in that (a) the active substance base is dissolved in a solvent, selected from among water and an aqueous buffer system with a pH between 4 and 8, preferably between 6 and 8, (b) the solution thus prepared is combined with an excess of the acid, preferably with 0.9 to 1.1 equivalents of the acid, and (c) the solvent is removed.

In the abovementioned process the solvent is preferably eliminated by spray-drying.

It was also found that the salts of the active substance BIBN4096 are characterised by an excellent solubility of >>1 mg/ml in water at a pH of 7. They are also characterised by special physical and physicochemical properties which lead to an improved pharmacological/pharmacokinetic activity when the substance is administered by inhalation.

The advantages are based on particular pharmacological/pharmacokinetic properties of certain salt forms of the active substance, which means that extensive and/or very rapid availability is ensured together with the very good solubility. The availability of the substance—both quantitative, based on the quantity of active substance administered, and also based on a high plasma level to be achieved as quickly as possible—is determined not only by the biochemical properties of the substance but also by physicochemical properties. If a solid is administered, as in the case of an inhalation powder, the parameters of absolute solubility in the ambient medium and also the speed of dissolution in the ambient medium as a function of the local concentration of the active substance and time should be taken into consideration in particular. Whereas on the other hand, for example for oral preparations in which the active substance is distributed as fast as possible in the ambient medium because of the formulation, the abovementioned parameters may optionally play a minor role on account of the low local concentration of the active substance and consequently these parameters are not controlled, or are only partly controlled, by the salt form, but are usually influenced by special formulations, these physical-chemical properties for inhalation powders are of great importance.

By further industrial processing, novel stable formulations of inhalation powders may be prepared from the abovementioned salts without the use of a carrier material. In principle, these salts by may converted by suitable micronising processes into a particle size of <10 μm, and are then made into the suitable form (powder mixture) for example by the addition of excipients, so as to ensure that the product has the required technical properties such as workability and stability. These powder mixtures may in principle be used in pre-metered systems (e.g. inhalettes) or in suitable multi-dose systems.

A third object of the present invention is the use of one of the abovementioned acid addition salts for preparing the inhalation powder according to the invention for the treatment of migraine.

It has surprisingly been found, according to the invention, that the salts of BIBN4096 can be morphologically changed by a spray-drying process in such a way that a powder thus produced can be transferred directly into a primary packaging means without any further steps, specifically without the need to mix it with a coarser carrier material and can be delivered from said packaging means for inhalation by means of a powder inhaler.

The manufacturing process may be controlled so that the particles are present in a suitable particle size, normally between 0.1 and 10 μm, and these particles have surface characteristics such that they are easy to fluidise/disperse.

It has also been found that the particle morphology including the particle size can be critically controlled by the choice of process parameters and manufacturing parameters. One surprising factor is that powders of this substance which have been micronised by "conventional" stream grinding processes and are present in a comparable particle size spectrum nevertheless differ fundamentally in their morphology from particles produced according to this invention, in terms of their surface characteristics/particle-to-particle interactions. This is apparent from the fact that the quality parameter known as the "Fine Particle Fraction of Delivered Dose" (e.g. according to the method of determining the "Aerodynamic Particle Size Distribution"-USP 24 or Pharm. Eur. Suppl. 2000) is improved by a factor 10 or more. As there is no need for a carrier material in the formulation either, the absolute dose of active substance actually available to the patient in a given total amount of powder administered is improved by a significantly higher factor.

The method of preparation according to the invention is characterised in that the active substance is suitably dissolved, sprayed and dried in a spray tower. The principle of spray-drying consists of breaking up a solution or suspension of the product which is to be dried into fine droplets and drying them with a hot gas current. The solid fraction remaining after the solvent has evaporated is separated off from the gas current by means of an inertia force separator (e.g. cyclone) and/or by a filter unit and collected. The microparticles thus produced are characterised by special values in terms of particle size, specific surface area and morphology.

Water or an aqueous buffer system with a pH between 6 and 8 have proved suitable as solvents. The active substance present in the form of a free base is dissolved according to the invention in the form of the corresponding salt in an aqueous solution which is combined with 0.9 to 1.1 equivalents of an acid, depending on the quantity of active substance to be dissolved. Preferred acids according to the invention are inorganic acids, such as for example hydrochloric acid, hydrobromic acid, phosphoric acid, nitric acid, sulphuric acid, carbonic acid, methanesulphonic acid or p-toluenesulphonic acid, fruit acids, such as for example citric acid, malic acid, tartaric acid, lactic acid, succinic acid or gluconic acid, carboxylic acids, such as for example formic acid, acetic acid, propionic acid or hexanoic acid, as well as other organic acids, such as for example oxalic acid, fumaric acid, mandelic acid or maleic acid, while the use of hydrochloric acid, hydrobromic acid or sulphuric acid and particularly the use of hydrochloric acid is of particular importance.

The adjustment of the active substance concentration is intended primarily to make the process economical. However, limits are imposed on the active substance concentration which may be selected, these limits being set by the fact that the surface qualities and morphology of the particles can be optimised by a specific ratio between the droplet size and solids concentration. Normally, a concentration of between 0.5 and 25% by weight, preferably between 1 and 20 percent by weight, most preferably between 2 and 10 percent by weight should be selected. The droplet size is a critical parameter for the production of inhalable particles. Depending on the nozzle used the throughput of spray gas should be selected in conjunction with the throughput of solution so as to achieve the desired droplet size. As there are a number of combinations of the parameters "nozzle—throughput of spray gas—throughput of solution" which result in a suitable droplet size, the process can sensibly be defined by the droplet size which is to be selected for the process. This may be characterised by the characteristic value $X_{50}$ (median value=particle size/droplet size, below which 50% of the quantity of particles are found, with regard to the volume distribution of the individual particles/droplets), which should be in the range between 1.5 μm and 30 μm, preferably between 1.5 μm and 20 μm, more preferably between 1.5 μm and 8 μm, as well as the characteristic value $Q_{(5.8)}$ (corresponding to the quantity of particles below 5.8 μm, based on the distribution by volume of the particles), which should be between 10% and 100%, preferably between 20% and 100% and most preferably between 50% and 100%.

On an industrial scale this is achieved by using a suitable commercial nozzle, e.g. single- or multi-substance nozzles which exhibit these characteristics as a function of the nozzle parameters (e.g. speed of rotation in the case of rotary atomisers or applied pressure and the resulting mass flow of the atomising gas in the case of two-substance nozzles) as well as the spray rate (volumetric flow of "spray solution"). Apart from the special conditions which have to be adhered to during the actual spraying process, in order to generate suitable droplets for the drying process, it is apparent that the surface characteristics of the particles may also be positively or deliberately influenced by the choice of the drying parameters. The critical characteristics which impinge on the drying step are the inlet and outlet temperature of the drying gas and the volumetric flow of the drying gas passed through. Care should be taken to ensure that the droplets of suitable size are passed through the drying chamber in such a way that the droplets and the dried particles do not come into contact, or only come into slight contact, with the wall of the spray tower. This is achieved by the use of nozzles with a corresponding spray cone, by a spray tower of suitable diameter and by the flow conditions in the apparatus. The starting temperature must be adapted to the process so that the powder has a sufficiently low residual solvent content and thus a sufficient chemical and physical stability is achieved. This is ideally obtained if the starting temperature is maintained in the region of the boiling temperature of the solvent or slightly above. By contrast, the inlet temperature of the drying gas must be selected so that in conjunction with the parameter "volumetric flow of drying gas" and the spray rate, the drying is gentle enough to produce particles with suitable surface qualities.

A fourth object of the invention is thus a process for preparing an inhalation powder, comprising the steps of
  (a) dissolving the active substance BIBN4096 in water or an aqueous buffer system with a pH of between 4 and 8, preferably between 6 and 8, containing an excess, preferably 0.9 to 1.1 equivalents, of a mineral acid or an organic acid, depending on the quantity of active substance which is to be dissolved, the active substance being converted into the corresponding salt,
  (b) spraying the resulting solution of active substance in conventional manner so as to obtain a spray mist with a droplet size having the characteristic value $X_{50}$ in the range from 1.5 to 30 μm, preferably from 1.5 to 20 μm, more preferably from 1.5 to 8 μm, and $Q_{(5.8)}$ between 10% and 100%, preferably between 20% and 100%, more preferably between 50% and 100%,
  (c) drying the spray mist thus obtained by means of a drying gas, while applying the following parameters:
    an inlet temperature of the drying gas of 100° C. to 350° C., preferably between 120° C. and 250° C. and more preferably between 130° C. and 200° C.,
    an outlet temperature of the drying gas of 40° C. to 120° C. (cf. Example),
    a volumetric flow of the spray gas of 1 $Nm^3$/h to 15 $Nm^3$/h,
    a volumetric flow of the drying gas of 15 $Nm^3$/h to 1500 $Nm^3$/h, preferably 15 $Nm^3$/h to 150 $Nm^3$/h, and
  (d) separating the dried solid fraction from the drying gas current in conventional manner.

The particles produced according to the invention have high physical stability. In particular, the properties of the particles when used as an inhalation powder enable a high proportion of fine particles to be realised, technically determined, for example, by cascade impactor measurement (Andersen Cascade Impactor, according to USP 24 or Pharm. Eur. Suppl. 2000). Typically, the proportion of the particles according to this method which are less than 5 μm in size (aerodynamically) is greater than 15%, while in some cases fine fractions of more than 50% are achieved. Apart from this key parameter for inhalable substances, the powder is characterised in that it can be further processed by current technical processes. Powders produced in this way are characterised by the physicochemical parameters of particle size, e.g. measured by laser diffraction, as well as specific surface, e.g. measured by multipoint B.E.T. measurement. For the characteristic value $Q_{(5.8)}$ the particle size of powders thus produced is typically between 50% and 100%, and for the parameter $X_{50}$ it is between 1 μm and 6 μm. Particles which are produced by the above methods typically have values for the specific surface of between 1 $m^2$/g and 20 $m^2$/g, ideally between 1 $m^2$/g and 10 $m^2$/g. Geometrically, particles produced by the above methods have particle shapes which may be described, depending on the test conditions, between the extremes of "spherical shape", "spherical shape with cavity, optionally with hole", "spherical shape with inwardly shaped convexities", as well as "collapsed hollow body". Under the scanning electron microscope the surface of such particles is substantially smooth or (spherically) nanostructured on the surface.

A fifth object of the present invention is thus an inhalation powder containing one of the abovementioned acid addition salts of the active substance base 1-[$N^2$-[3,5-dibromo-N-[[4-(3,4-dihydro-2(1H)-oxoquinazolin-3-yl)-1-piperidinyl]carbonyl]-D-tyrosyl]-L-lysyl]-4-(4-pyridinyl)-piperzine [BIBN4096] of formula (I) in the form of microparticles, characterised in that
  (a) the particles have a specific surface between 1 $m^2$/g and 20 $m^2$/g, preferably between 1 $m^2$/g and 10 $m^2$/g,
  (b) the characteristic value $Q_{(5.8)}$ is between 50% and 100% and
  (c) the parameter $X_{50}$ is between 1 μm and 6 μm.

A sixth object of the present invention is an inhalation powder, obtainable by the above-mentioned process according to the invention.

EXPERIMENTAL SECTION

1) Methods of Measurement

--- a) Determining the particle size by laser diffraction (Fraunhofer diffraction):

| | |
|---|---|
| Method of measurement: | In order to determine the particle size, the powder is placed in a laser diffraction spectrometer by means of a dispersing unit. By the median value $X_{50}$ is meant the particle size below which 50% of the particles are found. The $Q_{(5.8)}$ value describes the percentage proportion of the particles which are less than 5.8 μm in size. |
| Measuring equipment: | Laser diffraction spectrometer (HELOS), Messrs. Sympatec |
| Software: | WINDOX 4 |
| Dispersing unit: | RODOS/dispersing pressure: 3 bar |
| Focal length: | 100 mm [measuring range: 0.9 . . . 175 μm] |
| Evaluation mode: | HRLD (V 4) |

-continued b) Determining the specific surface:

| | |
|---|---|
| Method of measurement: | The specific surface is determined by exposing the powder sample to a nitrogen atmosphere at different pressures. Cooling the sample causes the nitrogen molecules to be condensed on the surface of the particles. The quantity of condensed nitrogen is determined by means of the pressure drop in the system and the specific surface of the sample is calculated by means of the surface nitrogen requirement and the weight of the sample. |
| Measuring equipment | Tri Star Multi Point BET, Messrs. Micromeritics |
| Heating station: | VacPrep 061, Messrs. Micromeritics |
| Heating: | about 12 h/40° C. |
| Analytical parameters | |
| Sample container: | ½ inch; with "filler rod" |
| Methods of analysis: | 16 point BET surface measurement 0.05 to 0.20 p/p0 |
| absolute pressure tolerance: | 5.0 mm Hg |
| relative pressure tolerance: | 5.0% |
| speed of evacuation: | 50.0 mm Hg/second |
| evacuation threshold: | 10.0 mm Hg |
| duration: | 0.1 h |
| void volume: | lowering of Dewar vessel, t: 0.5 h |
| retention time: | 20 seconds |
| Minimum equilibration time: | 600 seconds |
| Adsorbent: | nitrogen | c) Determining the droplet size by laser diffraction (according to Mie):

| | |
|---|---|
| Measuring equipment: | Laser diffraction spectrometer (HELOS), Messrs. Sympatec |
| Software: | WINDOX 4 |
| Focal length: | 100 mm [Measuring range: 0.9 . . . 175 µm] |
| Method of measurement: | The droplet size is determined by removing the nozzle from the spray drier and placing the spray in the upper third of the spray cone centrally in the laser beam. The measurement is taken at ambient temperature with water as the reference medium under otherwise identical conditions. |

2) Example of Spray Parameters

Example 1

Spray Parameter, Suitable for an Aqueous BIBN4096 Solution (Modified BÜCHI Spray Tower)

| | |
|---|---|
| Concentration solution | 10 g BIBN4096 in 100 ml of 0.115 mol/L HCl |
| Droplet size  $Q_{(5.8)}$ (Reference solution: H$_2$O at ambient temperature) | 71% |
| $X_{50}$ | 3.9 µm |
| volumetric flow "spray rate" | 9 ml/min |
| spray pressure (nozzle type) | 4.6 bar overpressure (N$_2$) (BÜCHI spray nozzle 0.7 mm, Art. No. 04364) |
| volumetric flow "atomising pressure" (nozzle type) | 2211 standard litre/h (BÜCHI spray nozzle 0.7 mm, Art. No. 04364) |
| Inlet temperature | 150° C. |
| Outlet temperature | 100° C. |
| volumetric flow "drying gas" | 30 standard m$^3$/h |
| cross section of drying tower | 105 mm |

Example 2

Spray Parameter Suitable for an Aqueous BIBN4096 Solution (Modified BÜCHI Spray Tower)

| | |
|---|---|
| Concentration solution | 9.1 g/100 g |
| solvent: | 0.115 mol/L HCl |
| Droplet size  $Q_{(5.8)}$ (Reference solution: H$_2$O at ambient temperature) | <10% |
| $X_{50}$ | 13 µm |
| volumetric flow "spray rate" | 0.54 L/h |
| spray pressure (nozzle type) | 1.0 bar overpressure (N$_2$) (BÜCHI spray nozzle 0.7 mm, Art. No. 04364) |
| Mass flow Spray gas nozzle type | 0.72 kg/h (BÜCHI spray nozzle 0.7 mm, Art. No. 04364) |
| Inlet temperature | 150° C. |
| Outlet temperature | 104° C. |
| volumetric flow "drying gas" | 35–36 standard m$^3$/h |
| cross section of drying tower | 105 mm |

Example 3

Spray Parameter Suitable for an Aqueous BIBN4096 Solution (Modified BÜCHI Spray Tower)

| | |
|---|---|
| Concentration solution | 4.0 g/100 g |
| solvent: | 0.05 mol/L HCl |
| Droplet size  $Q_{(5.8)}$ | 69% |
| (Reference solution: $H_2O$ at ambient temperature) | |
| $X_{50}$ | 5 μm |
| volumetric flow "spray rate" | 0.63 L/h |
| spray pressure | 6.1 bar |
| (nozzle type) | overpressure ($N_2$) |
| | (BÜCHI spray nozzle 0.7 mm, Art. No. 04364) |
| Mass flow Spray gas | 3.4 kg/h |
| (nozzle type) | (BÜCHI spray nozzle 0.7 mm, Art. No. 04364) |
| Inlet temperature | 150° C. |
| Outlet temperature | 98–99° C. |
| volumetric flow "drying gas" | 35 standard m³/h |
| cross section of drying tower | 105 mm |

Example 4

Spray Parameter Suitable for an Aqueous BIBN4096 Solution (Modified BÜCHI Spray Tower)

| | |
|---|---|
| Concentration solution | 10.3 g/100 g |
| solvent: | 0.13 mol/L HCl |
| Droplet size  $Q_{(5.8)}$ | 69% |
| (Reference solution: $H_2O$ at ambient temperature) | |
| $X_{50}$ | 5 μm |
| volumetric flow "spray rate" | 0.63 L/h |
| spray pressure | 6.1–6.2 bar |
| (nozzle type) | overpressure ($N_2$) |
| | (BÜCHI spray nozzle 0.7 mm, Art. No. 04364) |
| Mass flow Spray gas nozzle type | 3.4 kg/h |
| | (BÜCHI spray nozzle 0.7 mm, Art. No. 04364) |
| Inlet temperature | 150° C. |
| Outlet temperature | 98–101° C. |
| volumetric flow "drying gas" | 35 standard m³/h |
| cross section of drying tower | 105 mm |

Example 5

Spray Parameter Suitable for an Aqueous BIBN4096 Solution (Modified BÜCHI Spray Tower)

| | |
|---|---|
| Concentration solution | 2 g/100 g |
| solvent: | 0.012 mol/L sulphuric acid |
| Droplet size  $Q_{(5.8)}$ | 39% |
| (Reference solution: $H_2O$ at ambient temperature) | |
| $X_{50}$ | 7.0 μm |
| volumetric flow "spray rate" | 0.54 L/h |
| spray pressure | 3.3–3.5 bar |
| (nozzle type) | overpressure ($N_2$) |
| | (BÜCHI spray nozzle 0.7 mm, Art. No. 04364) |

-continued

| | |
|---|---|
| Mass flow Spray gas nozzle type | 2.1 kg/h |
| | (BÜCHI spray nozzle 0.7 mm, Art. No. 04364) |
| Inlet temperature | 150° C. |
| Outlet temperature | 101° C. |
| volumetric flow "drying gas" | 35 standard m³/h |
| cross section of drying tower | 105 mm |

Example 6

Spray Parameter Suitable for an Aqueous BIBN4096 Solution (Modified BÜCHI Spray Tower)

| | |
|---|---|
| Concentration solution | 5 g/100 g |
| solvent: | 0.02 mol/L citric acid |
| Droplet size  $Q_{(5.8)}$ | 55% |
| (Reference solution: $H_2O$ at ambient temperature) | |
| $X_{50}$ | 5.5 μm |
| volumetric flow "spray rate" | 0.54 L/h |
| spray pressure | 4.4–4.6 bar |
| (nozzle type) | overpressure ($N_2$) |
| | (BÜCHI spray nozzle 0.7 mm, Art. No. 04364) |
| Mass flow Spray gas nozzle type | 2.8 kg/h |
| | (BÜCHI spray nozzle 0.7 mm, Art. No. 04364) |
| Inlet temperature | 150° C. |
| Outlet temperature | 99° C. |
| volumetric flow "drying gas" | 35 standard m³/h |
| cross section of drying tower | 105 mm |

Example 7

Spray Parameter Suitable for an Aqueous BIBN4096 Solution (Modified BÜCHI Spray Tower)

| | |
|---|---|
| Concentration solution | 10 g/100 g |
| solvent: | 0.06 mol/L tartaric acid |
| Droplet size  $Q_{(5.8)}$ | 60% |
| (Reference solution: $H_2O$ at ambient temperature) | |
| $X_{50}$ | 5.3 μm |
| volumetric flow "spray rate" | 0.54 L/h |
| spray pressure | 4.7–4.9 bar |
| (nozzle type) | overpressure ($N_2$) |
| | (BÜCHI spray nozzle 0.7 mm, Art. No. 04364) |
| Mass flow Spray gas nozzle type | 3 kg/h |
| | (BÜCHI spray nozzle 0.7 mm, Art. No. 04364) |
| Inlet temperature | 150° C. |
| Outlet temperature | 101° C. |
| volumetric flow "drying gas" | 35 standard m³/h |
| cross section of drying tower | 105 mm |

Example 8

Spray Parameter Suitable for an Aqueous BIBN4096 Solution (Modified BÜCHI Spray Tower)

| | |
|---|---|
| Concentration solution | 20 g/100 g |
| solvent: | 0.26 mol/L HBr |
| Droplet size $Q_{(5.8)}$ | 69% |
| (Reference solution: $H_2O$ at ambient temperature) | |
| $X_{50}$ | 5.1 μm |
| volumetric flow "spray rate" | 0.54 L/h |
| spray pressure | 6 bar |
| (nozzle type) | overpressure ($N_2$) (BÜCHI spray nozzle 0.7 mm, Art. No. 04364) |
| Mass flow Spray gas nozzle type | 3.4 kg/h (BÜCHI spray nozzle 0.7 mm, Art. No. 04364) |
| Inlet temperature | 150° C. |
| Outlet temperature | 100° C. |
| volumetric flow "drying gas" | 35 standard m³/h |
| cross section of drying tower | 105 mm |

Example 9

Spray Parameter Suitable for an Aqueous BIBN4096 Solution (Modified BÜCHI Spray Tower)

| | |
|---|---|
| Concentration solution | 5 g/100 g |
| solvent: | 0.06 mol/L methanesulphonic acid |
| Droplet size $Q_{(5.8)}$ | 69% |
| (Reference solution: $H_2O$ at ambient temperature) | |
| $X_{50}$ | 5.1 μm |
| volumetric flow "spray rate" | 0.54 L/h |
| spray pressure | 6 bar |
| (nozzle type) | overpressure ($N_2$) (BÜCHI spray nozzle 0.7 mm, Art. No. 04364) |
| Mass flow Spray gas nozzle type | 3.4 kg/h (BÜCHI spray nozzle 0.7 mm, Art. No. 04364) |
| Inlet temperature | 150° C. |
| Outlet temperature | 100° C. |
| volumetric flow "drying gas" | 35 standard m³/h |
| cross section of drying tower | 105 mm |

3) Characterisation of the Solid Particles Obtained from One of the Abovementioned Examples

Example 1

| | | |
|---|---|---|
| Particle size | $X_{50}$ | 2.5 μm |
| | $Q_{(5.8)}$ | 97% |

Example 2

| | | |
|---|---|---|
| Particle size | $X_{50}$ | 5.5 μm |
| | $Q_{(5.8)}$ | 53.3% |
| Specific Surface | $S_m$ | 1.9 m²/g |

Example 3

| | | |
|---|---|---|
| Particle size | $X_{50}$ | 2.4 μm |
| | $Q_{(5.8)}$ | 96.7% |
| Specific Surface | $S_m$ | 5.0 m²/g |

Example 4

| | | |
|---|---|---|
| Particle size | $X_{50}$ | 3.0 μm |
| | $Q_{(5.8)}$ | 90.0% |
| Specific Surface | $S_m$ | 3.4 m²/g |

Figure 1:
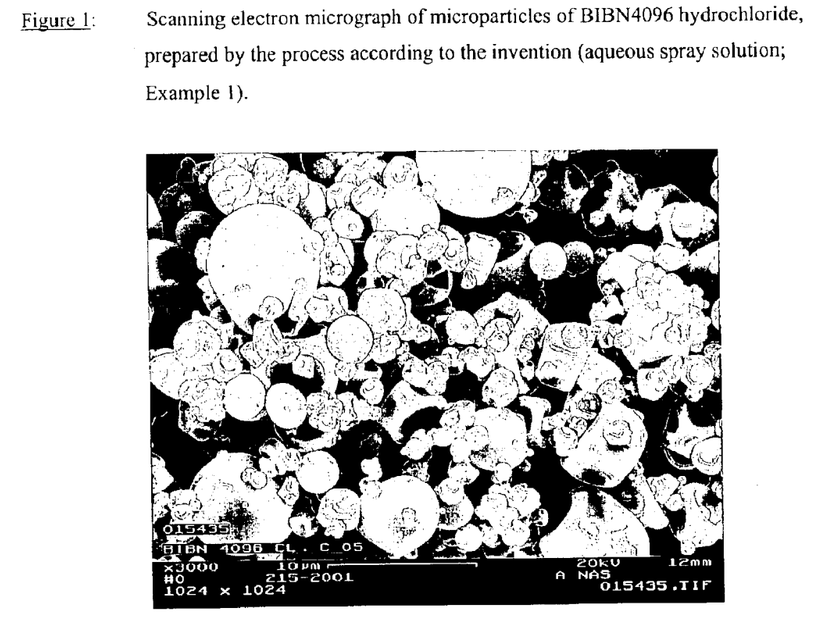
FIGS. 1 to 4 show scanning electron microscope photographs of microparticles prepared from some of the abovementioned Examples by the method according to the invention from an aqueous spray solution.
Figure 2:
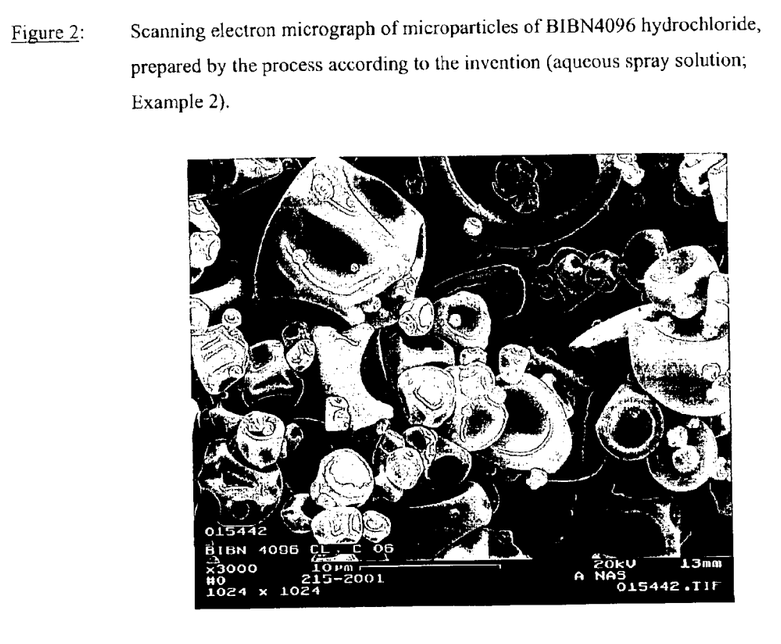
Figure 3:
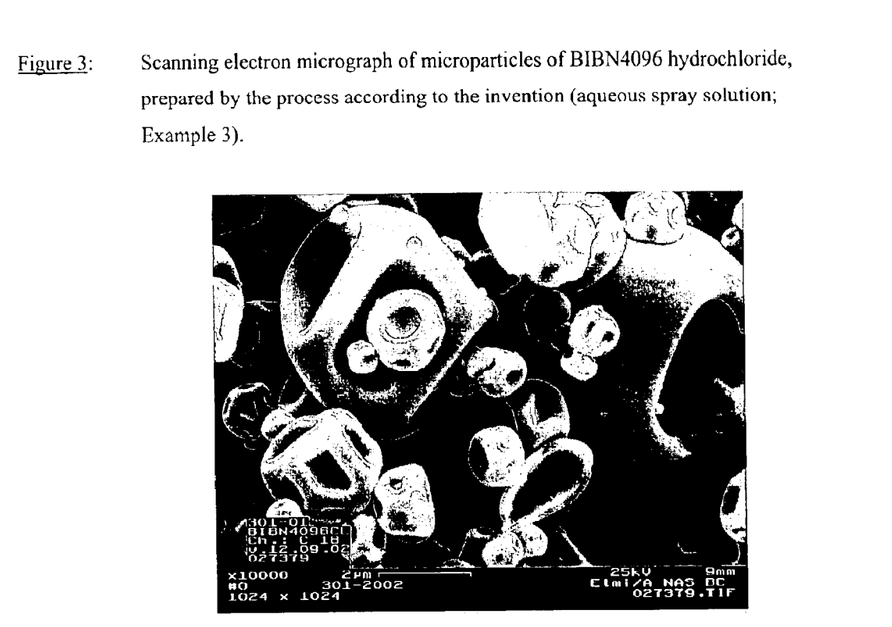
Figure 4:
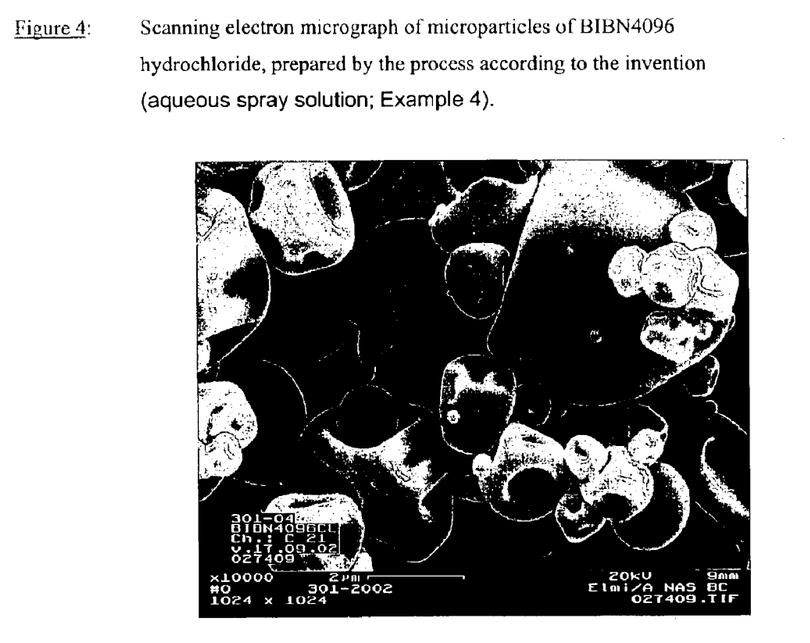

What is claimed is:

1. A process for preparing an acid addition salt of 1-[N2-[3,5-dibromo-N-[[4-(3,4-dihydro-2(1H)-oxoquinazolin-3-yl)-1-piperidinyl]carbonyl]-D-tyrosyl]-L-lysyl]-4-(4-pyridinyl)-piperazine, which has the formula (I)

the process comprising the following steps:
(a) dissolving 1-[N2-[3,5-dibromo-N-[[4-(3,4-dihydro-2 (1H)-oxoquinazolin-3-yl)-1-piperidinyl]carbonyl]-D-tyrosyl]-L-lysyl]-4-(4-pyridinyl)-piperazine (the base) in water or an aqueous buffer system with a pH between 4 and 8,
(b) combining the solution of step (a) thus prepared with an excess of an acid, and
(c) removing the solvent by spray-drying.

2. The process according to claim 1, wherein the pH of the aqueous buffer system is between 6 and 8.

3. The process according to claim 1, wherein the acid of step (b) is present in an amount of 0.9 to 1.1 equivalents.

4. A process for preparing an inhalation powder, comprising the steps of (a) dissolving a pharmaceutically acceptable acid addition salt of 1-[N2-[3,5-dibromo-N-[[4-(3,4-dihydro-2(1H)-oxoquinazolin-3-yl)-1-piperidinyl]carbonyl]-D-tyrosyl]-L-lysyl]-4-(4-pyridinyl)-piperazine in water, or 1-[N2-[3,5-dibromo-N-[[4-(3,4-dihydro-2(1H)-oxoquinazolin-3-yl)-1-piperidinyl]carbonyl]-D-tyrosyl]-L-lysyl]-4-(4-pyridinyl)-piperazine in an aqueous system containing an excess of a mineral acid or an organic acid, depending, whereby it is converted into a corresponding pharmaceutically acceptable salt, (b) spraying the resulting solution of the salt from step (a) so as to obtain a spray mist with a droplet size having the characteristic value $X_{50}$ in the range from 1.5 to 30 μm, and (c) obtaining dried particles by drying the spray mist of step (b) by means of a drying gas, while applying the following parameters:
   (1) an inlet temperature of the drying gas of 100° C. to 350° C.,
   (2) an outlet temperature of the drying gas of 40° C. to 120° C.,
   (3) a volumetric flow of the spray mist of 1 $Nm^3/h$ to 15 $Nm^3/h$, and
   (4) a volumetric flow of the drying gas of 15 $Nm^3/h$ to 1500 $Nm^3/h$.

5. The process according to claim 4, wherein the solution of the salt from step (a) has a concentration of 0.5 to 25% by weight.

6. The process according to claim 4, wherein the solution of the salt from step (a) has a concentration of 1 to 20% by weight.

7. The process according to claim 4, wherein the solution of the salt from step (a) has a concentration of 2 to 10% by weight.

8. The process according to claim 4, wherein the droplet size of step (b) has the characteristic value $X_{50}$ in the range from 1.5 to 8 μm.

9. The process according to claim 4, wherein the droplet size of step (b) has the characteristic value $Q_{(5.8)}$ in the range from 50% to 100%.

10. The process according to claim 4, wherein the dried particles obtained from step (c) have a specific surface of between 1 $m^2/g$ and 20 $m^2/g$.

11. The process according to claim 4, wherein the dried particles obtained from step (c) have a specific surface of between 1 $m^2/g$ and 10 $m^2/g$.

12. The process according to claim 4, wherein the volumetric flow of the drying gas is 15 $Nm^3/h$ to 150 $Nm^3/h$.

13. A process for preparing a powder, comprising the steps of:

(a) dissolving a pharmaceutically acceptable acid addition salt of 1-[N2-[3,5-dibromo-N-[[4-(3,4-dihydro-2(1H)-oxoquinazolin-3-yl)-1-piperidinyl]carbonyl]-D-tyrosyl]-L-lysyl]-4-(4-pyridinyl)-piperazine in water, or 1-[N2-[3,5-dibromo-N-[[4-(3,4-dihydro-2(1H)-oxoquinazolin-3-yl)-1-piperidinyl]carbonyl]-D-tyrosyl]-L-lysyl]-4-(4-pyridinyl)-piperazine in an aqueous system containing an excess of a mineral acid or an organic acid, whereby it is converted into a corresponding pharmaceutically acceptable salt, (b) spraying the resulting solution of the salt from step (a) so as to obtain a spray mist with a droplet size having the characteristic value $X_{50}$ in the range from 1.5 to 30 μm, (c) drying the spray mist so as to obtain dried particles.

14. The process according to claim 13, wherein the aqueous system has a pH between 6 and 8.

15. The process according to claim 13, wherein the acid of step (a) is present in an amount of 0.9 to 1.1 equivalents.

16. The process according to claim 13, wherein the droplet size of step (b) has the characteristic value $X_{50}$ in the range from 1.5 to 8 μm.

17. The process according to claim 13, wherein the droplet size of step (b) has the characteristic value $Q_{(5.8)}$ in the range from 50% to 100%.

18. The process according to claim 13, wherein the dried particles obtained from step (c) have a specific surface of between 1 $m^2/g$ and 10 $m^2/g$.

19. The process according to claim 13, wherein the spray mist is dried by means of a drying gas, while applying the following parameters:
   (1) an inlet temperature of the drying gas of 100° C. to 350° C.,
   (2) an outlet temperature of the drying gas of 40° C. to 120° C.,
   (3) a volumetric flow of the spray mist of 1 $Nm^3/h$ to 15 $Nm^3/h$, and
   (4) a volumetric flow of the drying gas of 15 $Nm^3/h$ to 1500 $Nm^3/h$.

20. The process according to claim 19, wherein the volumetric flow of the drying gas is 15 $Nm^3/h$ to 150 $Nm^3/h$.

* * * * *